United States Patent [19]
Matsumoto et al.

[11] Patent Number: 5,524,628
[45] Date of Patent: Jun. 11, 1996

[54] ULTRASONIC DIAGNOSTIC SYSTEM

[75] Inventors: Kazuhiro Matsumoto; Etsuro Machida, both of Kawasaki, Japan

[73] Assignee: Fujitsu Limited, Kawasaki, Japan

[21] Appl. No.: 456,927

[22] Filed: Jun. 1, 1995

[30] Foreign Application Priority Data

Oct. 31, 1994 [JP] Japan ................................. 6-266728

[51] Int. Cl.$^6$ .................................................... A61B 8/00
[52] U.S. Cl. ................. 128/661.01; 128/660.05; 128/661.08
[58] Field of Search .................. 128/660.04, 660.05, 128/660.08, 661.01, 661.08, 661.09, 661.10, 662.01

[56] References Cited

U.S. PATENT DOCUMENTS 5,148,810 9/1992 Maslak et al. .............. 128/661.01
5,301,674 4/1994 Erikson et al. ............. 128/661.01

*Primary Examiner*—George Manuel
*Attorney, Agent, or Firm*—Staas & Halsey

[57] ABSTRACT

There is provided an ultrasonic diagnostic system capable of contributing to simplification in operation throughout the color flow imaging. The ultrasonic diagnostic system is provided with a focus-follow means for providing such a control that a movement of a domain of interest involves a movement of at least focus involved in the transmitting side between the focus involved in the transmitting side and the focus involved in the receiving side.

3 Claims, 3 Drawing Sheets

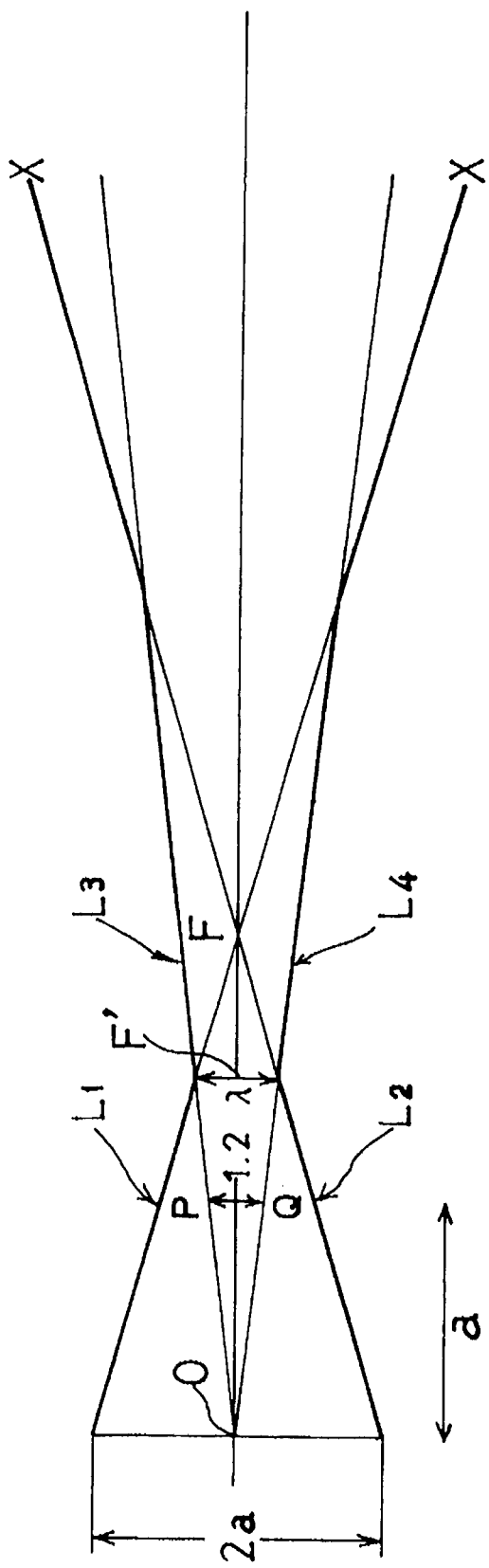

ULTRASONIC DIAGNOSTIC SYSTEM

BACKGROUND OF THE INVENTION

1. Field of the Invention

The present invention relates to an ultrasonic diagnostic system provided with a so-called color flow image function in which a color image representative of a blood flow distribution is formed.

2. Description of the Related Art

There has been used an ultrasonic diagnostic system which is available with the diagnosis of diseases through displaying an ultrasonic tomographic image (B-mode image) within the subject and the human body particularly on the basis of ultrasonic wave signals obtained by means of transmitting ultrasonic beams within the human body and receiving the ultrasounds reflected by a tissue in the human body.

Recently, such an ultrasonic diagnostic system is equipped with a color flow image function in which a blood flow distribution within the subject is detected utilizing a Doppler effect, and blood flow information superposed on the B-mode image is displayed with a coloring such that a blood flow, which flows in a predetermined direction, is colored by, for example, red and a blood flow, which flows in the opposite direction, is colored by, for example, blue. A blood flow distribution can be detected in such a manner that a domain of interest for a blood flow distribution is set up on the B-mode image by a domain setting handler such as a track ball or the like, a line drawing representing the domain of interest set up is displayed on the B-mode image so that the blood flow distribution within the domain of interest can be detected. A color image representative of the blood flow distribution thus detected is superposed on the B-mode image and displayed.

When the blood flow distribution is observed using the above-mentioned color flow image function, it happens that only set up of the domain of interest on the B-mode image brings about a poor quality of image within the domain of interest and/or a poor sensitivity. It is only possible to observe the color image representative of the blood flow distribution within the domain of interest, when a focus of the ultrasonic beam is set within the domain of interest.

According to the conventional system, as described above, there is a need to perform both setting of the domain of interest and setting of the focus. This causes a troublesomeness in operation.

In view of the foregoing, it is an object of the present invention to provide an ultrasonic diagnostic system capable of contributing to simplification in operation throughout the color imaging.

SUMMARY OF THE INVENTION

To attain the above-mentioned object of the invention, according to the present invention, there is provided an ultrasonic diagnostic system comprising:

(1) ultrasonic transmitter-receiver means for transmitting ultrasonic beams, wherein a focus involved in a transmitting side is formed on a predetermined point within a subject, to an inside of the subject, and providing such a processing that ultrasonic beams reflected within the subject are received and a focus involved in a receiving side is formed on a predetermined point within the subject, thereby generating received signals each representative of intensity of reflection of the ultrasonic wave on an associated point on the ultrasonic beam extending inside the subject;

(2) B-mode image forming means for forming a B-mode image on the basis of the received signals obtained with said ultrasonic transmitter-receiver means;

(3) a domain setting handler for setting up a domain of interest for a blood flow distribution within the B-mode image;

(4) color flow imaging means for forming a color image representative of the blood flow distribution within said domain of interest on the basis of the received signals obtained with said ultrasonic transmitter-receiver means;

(5) display means for displaying the color image within said domain of interest, which is formed with said color flow imaging means, with the superposition thereof upon the B-mode image formed with said B-mode image forming means; and (6) focus-follow means for providing such a control that a movement of said domain of interest by operation of said domain setting handler involves a movement of at least focus involved in the transmitting side between the focus involved in the transmitting side and the focus involved in the receiving side.

In the ultrasonic diagnostic system according to the present invention, as mentioned above, it is preferable that the system further comprises a focus setting handler for setting at least focus involved in the transmitting side between the focus involved in the transmitting side and the focus involved in the receiving side to an optional position in depth within said domain of interest. In this case, it is preferable that said focus setting handler is adapted to set up a number of focal setting stages on a switching basis.

Since the ultrasonic diagnostic system according to the present invention is provided with the focus-follow means as defined in the above-referenced item (6), a movement of the domain of interest involves automatically a movement of a focus. Therefore, according to the present invention, the operation is simplified, and in addition a quality of image and a sensitivity are improved. Thus, it is possible to contribute to reduction of a diagnostic time and providing a high precision of diagnosis.

BRIEF DESCRIPTION OF THE DRAWINGS

FIG. 4 is a view for use in explanation of one technique for calculation of a focal position.

DESCRIPTION OF THE PREFERRED EMBODIMENTS

Hereinafter, there will be described embodiments of the present invention.

Figure 1:
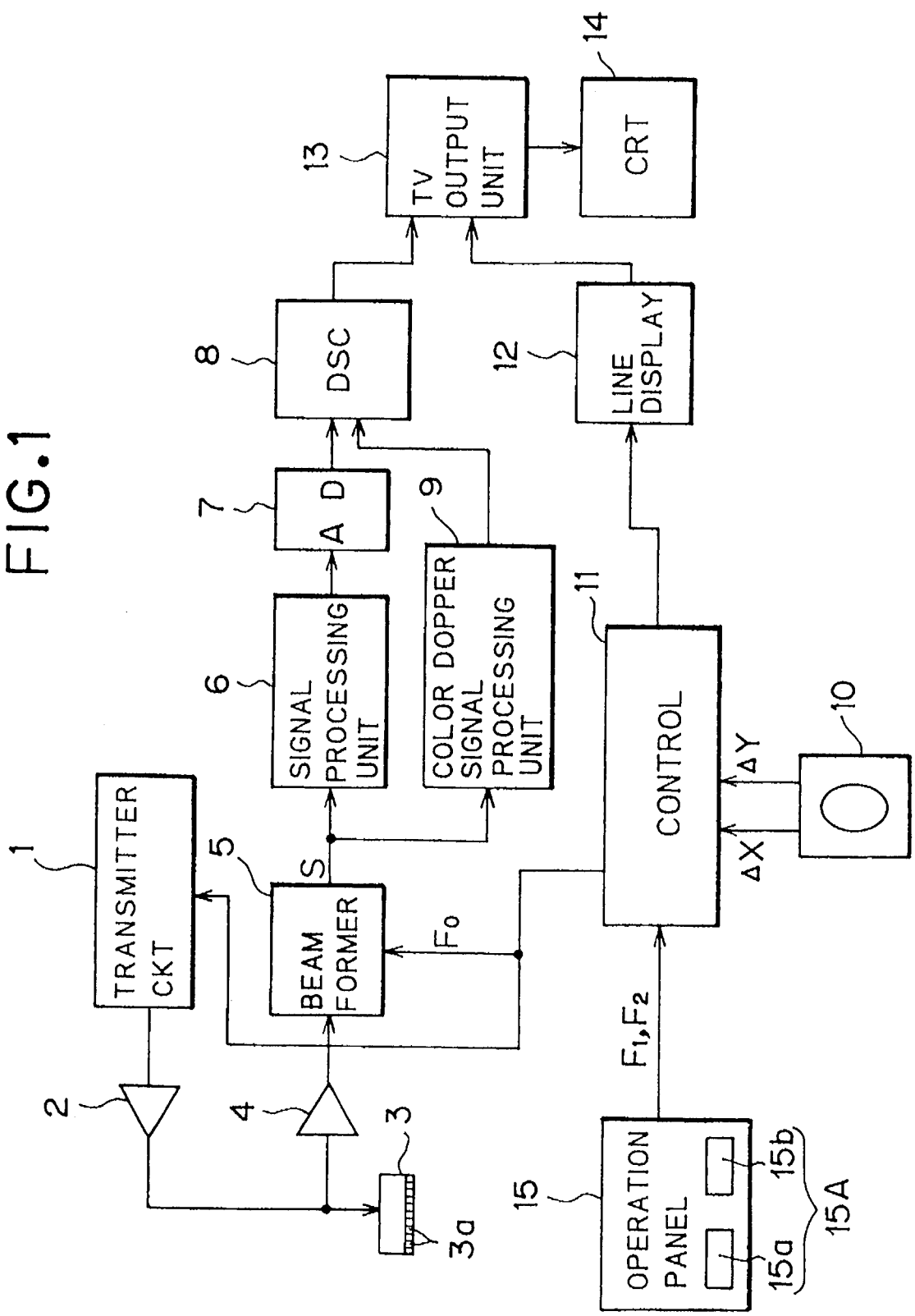
FIG. 1 is a block diagram of an ultrasonic diagnostic system according to an embodiment of the present invention.

FIG. 1 is a block diagram of an ultrasonic diagnostic system according to an embodiment of the present invention. The first embodiment of the present invention will be explained referring to FIG. 1, hereinafter.

Transmitter circuit 1 generates a plurality of pulses for ultrasonic wave transmission, which are subjected to timing regulation such that a focus involved in the transmission side is formed at a predetermined point inside the subject (not illustrated). The pulses for ultrasonic wave transmission are amplified in an amplifier 2 and converted into high voltage pulses, and then applied to a plurality of ultrasonic transducers 3a which constitute a probe 3. Ultrasonic beams are transmitted from the plurality of ultrasonic transducers 3a toward the inside of the subject.

The ultrasonic acoustic waves transmitted inside the subject are reflected on the respective points along the ultrasonic beams within the subject and return to the probe 3 so that the reflected ultrasounds are received by a plurality of ultrasonic transducers 3a. The ultrasound signals received by the plurality of ultrasonic transducers 3a are amplified in an amplifier 4 and then applied to a beamformer 5. In the beamformer 5, the ultrasound signals received by the plurality of ultrasonic transducers are each delayed with an associated suitable delay amount and are added, or beamformed, thereby forming received signals S each representative of intensity of reflection of the ultrasonic wave on the associated point on the ultrasonic beam wherein a focus involved in the receiving side is formed on a predetermined point within the subject.

The received signal S is processed in a signal processing unit 6 which serves to perform signal processing such as logarithmic compression, detection and the like, and thereafter subjected to an analog to digital (A/D) conversion in an A/D converter 7, and then converted into a TV signal in a digital scan converter (DSC) 8 as a B-mode image. Whereas the received signal S is applied also to a color Doppler signal processing unit 9 so as to be converted into a color Doppler signal. The converted color Doppler signal is applied to the digital scan converter (DSC) 8 so as to be converted into the TV signal.

An operator operates a track ball 10, which is an example of a domain setting handler, to set up a domain of interest in which a blood flow velocity is to be displayed.

Displacements $\Delta X$ and $\Delta Y$, which are involved in directions X and Y of the track ball 10, respectively, are inputted to a control unit 11 in which depth of a color start/termination and scan line number of a color start/termination are determined on the basis of a color domain depth factor representative of width in a depth direction of a domain of interest and a color scan factor representative of width in a scan direction of a domain of interest, which are set up beforehand, respectively. Those kinds of information are inputted to a line display unit 12 so as to be converted into a line signal indicative of a domain of interest. A TV output unit 13 receives the B-mode signal and the color Doppler signal outputted from the digital scan converter 8, and the line signal outputted from the line display unit 12. Those signals are displayed in their combination on a CRT 14.

The control unit 11 selects a focus setting feasible point of an ultrasonic beam which is closest to the position of, for example, one quarter of depth of a color start/termination from a shallow portion thereof, and transmits focus setting information F of the ultrasonic beam to the transmitter circuit 1 and the beamformer 5. Upon receipt of the focus setting information F, the transmitter circuit 1 sets up a focal position, which is involved in the transmitting side, of the ultrasonic beam transmitted from the probe 3. The beamformer 5 sets up a focal position of the ultrasonic beam involved in the receiving side.

Figure 2:
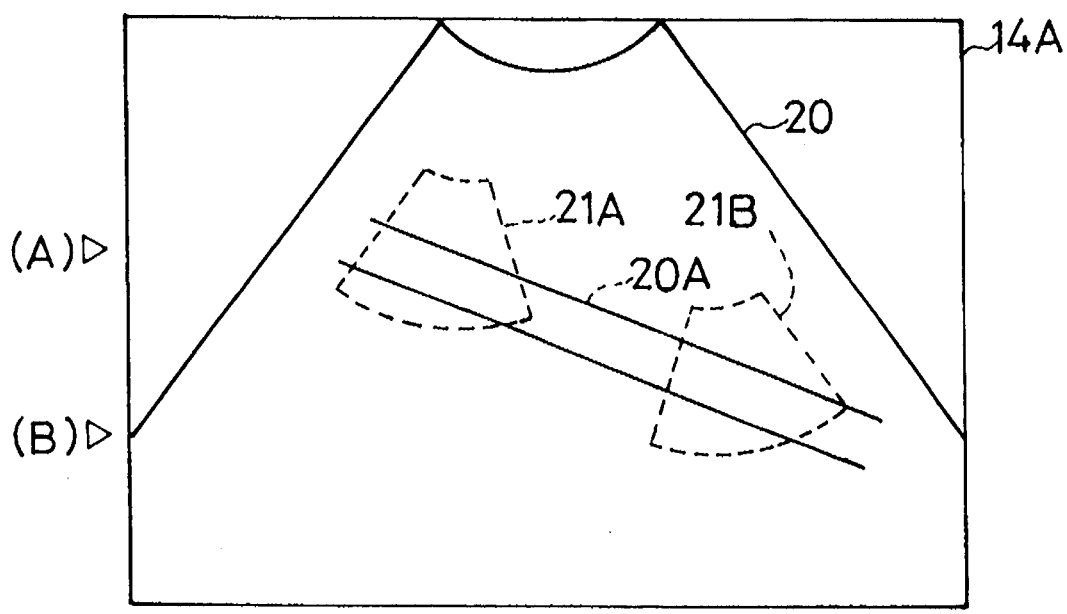
FIG. 2 is a typical illustration of an image displayed on a CRT.

FIG. 2 is a typical illustration of an image displayed on a CRT 14.

On a CRT display screen 14A, there is displayed a substantially fan-like shaped B-mode image 20 on which an image 20A of a blood vessel is displayed.

Further, on the display screen 14A, there are displayed domains 21A and 21B of interest, which are of similar figures to the appearance of the B-mode image 20, based on the line signal generated in the line display unit 12 through operation of the track ball 10 by an operator. It is noted that these two domains 21A and 21B of interest are not simultaneously displayed on the display screen 14A. For example, first, the domain 21A of interest is displayed. And when an operator operates the track ball 10, the displayed domain 21A of interest moves to a position of the domain 21B of interest. When a domain of interest is set to the domain 21A of interest shown in FIG. 2, the focus of the ultrasonic beam involved in transmitting and receiving is set to a position (A) in depth. When the domain of interest moves to the domain 21B of interest, the focus of the ultrasonic beam involved in transmitting and receiving also moves to a position (B) in depth. In this manner, the movement of the domain of interest involves the movement of the focus.

Returning to FIG. 1, the explanation will be continued.

An operator may operate a focus ratio setting handler 15a which is a component of a focus setting handler 15A on an operation panel 15 so as to set up a focal position of the ultrasonic beam between the upper end (edge portion at the shallow side in depth) and the lower end (edge portion at the deep side in depth) of the domain of interest with an optional ratio. An output $F_1$ of the focus ratio setting handler 15a is inputted to the control unit 11. Upon receipt of the output $F_1$ of the focus ratio setting handler 15a, the control unit 11 calculates the focal position selected by the user on the basis of depth of a color start/termination (coordinates of a direction in depth of a domain of interest) which is obtained through totalizing the outputs of the track ball 10. Further, the control unit 11 selects a focus setting feasible point of an ultrasonic beam which is closest to the focal position thus calculated, and transmits focus setting information $F_0$ of the ultrasonic beam to the transmitter circuit 1 and the beamformer 5. Upon receipt of the focus setting information $F_0$, the transmitter circuit 1 sets up a focal position, which is involved in the transmitting side, of the ultrasonic beam, and the beamformer 5 sets up a focal position of the ultrasonic beam involved in the receiving side.

The operation panel 15 is also provided with a focus stages setting handler 15b which is also a component of the focus setting handler 15A for setting the number of stages of focus within a domain of interest. Thus, an operator may set up a plurality of focal points within the domain of interest through operation of the focus stages setting handler.

Figure 3:
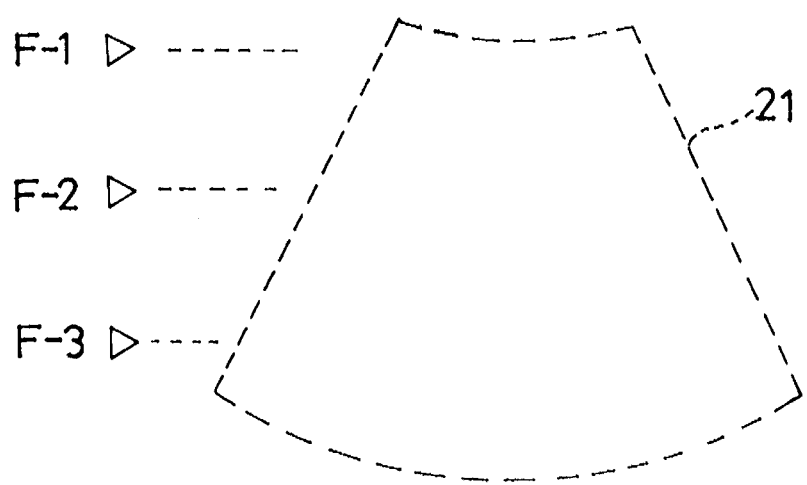
FIG. 3 is a typical illustration of an example in which three stages of focus are set up within a domain of interest.

FIG. 3 is a typical illustration of an example in which three stages of focus are set up within a domain of interest.

In this example, there are set up focal points F-1, F-2 and F-3 at the upper portion, the center and the lower portion of the domain 21 of interest, respectively. Positions in depth of the focal points F-1, F-2 and F-3 may be set up and moved through operation of the above-mentioned focus ratio setting handler 15a.

Information $F_2$, which is representative of the number of focus stages set by the focus stages setting handler 15b, is also inputted to the control unit 11. Upon receipt of information $F_2$, the control unit 11 calculates the focal position on the basis of both the information $F_2$ and the information $F_1$ outputted from the focus ratio setting handler 15a, and then transmits the focus setting information $F_0$ of the ultrasonic beam to the transmitter circuit 1 and the beamformer 5.

Next, there will be explained exemplarily one technique for calculation of a focal position. It is noted that the present invention is not restricted to the technique for calculation of a focal position as described below.

FIG. 4 is a view for use in explanation of one technique for calculation of a focal position by way of example.

When a transmitting and receiving aperture for ultrasonic acoustic waves is denoted by $2a$, straight lines $L_1$ and $L_2$, which couple both edges of the aperture with a focal point F, respectively, are drawn. In addition, straight lines $L_3$ and $L_4$, which couple the center O of the transmitting and receiving aperture for ultrasonic acoustic waves with points P and Q, respectively, are drawn, where the points P and Q are each by a distance a away from a transmitting and receiving plane with respect to the vertical direction to a direction in which the transmitting and receiving plane is extended, and in addition are located at the places shifted by $\pm 0.6\lambda$ ($\lambda$ denotes the central wave-length of the ultrasonic acoustic wave) from the center of the transmitting and receiving aperture toward both the ends thereof, respectively. The outside lines (illustrated with the thick lines) of the straight lines $L_1$, $L_3$ and $L_2$, $L_4$ define a substantial beam pattern.

It is preferable to select a focus in such a manner that the position F' of the finest beam is located in the center of the color domain. Incidentally, it is acceptable to select a focus in such a manner that a geometric focus F is located at a predetermined position.

While the present embodiment shows an example in which the movement of the domain of interest involves the movement of both the focus involved in the transmitting side and the focus involved in the receiving side, it is possible to expect a remarkable improvement in a quality of image and a sensitivity even when it is so arranged that the movement of the domain of interest involves the movement of only the focus involved in the transmitting side.

As described above, according to the present invention, the operation is simplified, and in addition a quality of image and a sensitivity are improved. Thus, it is possible to contribute to reduction of a diagnostic time and providing a high precision of diagnosis.

The present invention is not limited to the particular embodiments described above. Various changes and modifications may be made within the spirit and scope of the invention.

We claim:

1. An ultrasonic diagnostic system comprising:

ultrasonic transmitter-receiver means for transmitting ultrasonic beams, wherein a focus involved in a transmitting side is formed on a predetermined point within a subject, to an inside of the subject, and providing such a processing that ultrasonic beams reflected within the subject are received and a focus involved in a receiving side is formed on a predetermined point within the subject, thereby generating received signals each representative of intensity of reflection of the ultrasonic wave on an associated point on the ultrasonic beam extending inside the subject;

B-mode image forming means for forming a B-mode image on the basis of the received signals obtained with said ultrasonic transmitter-receiver means;

a domain setting handler for setting up a domain of interest for a blood flow distribution within the B-mode image;

color flow imaging means for forming a color image representative of the blood flow distribution within said domain of interest on the basis of the received signals obtained with said ultrasonic transmitter-receiver means;

display means for displaying the color image within said domain of interest, which is formed with said color flow imaging means, with the superposition thereof upon the B-mode image formed with said B-mode image forming means; and focus-follow means for providing such a control that a movement of said domain of interest by operation of said domain setting handler involves a movement of at least focus involved in the transmitting side between the focus involved in the transmitting side and the focus involved in the receiving side.

2. A system according to claim 1, further comprising a focus setting handler for setting at least focus involved in the transmitting side between the focus involved in the transmitting side and the focus involved in the receiving side to an optional position in depth within said domain of interest.

3. A system according to claim 2, wherein said focus setting handler serves to set up a number of focal setting stages on a switching basis.

* * * * *

UNITED STATES PATENT AND TRADEMARK OFFICE
CERTIFICATE OF CORRECTION

PATENT NO. : 5,524,628
DATED : June 11, 1996
INVENTOR(S) : Kazuhiro MATSUMOTO et al.

It is certified that error appears in the above-indentified patent and that said Letters Patent is hereby corrected as shown below:

Column 5, line 14, delete "a", second occurrence, and insert therefor --a--.

Signed and Sealed this

Twenty-ninth Day of October 1996

Attest:

BRUCE LEHMAN

Attesting Officer

Commissioner of Patents and Trademarks